US009933849B2

(12) United States Patent
Rezaee et al.

(10) Patent No.: US 9,933,849 B2
(45) Date of Patent: Apr. 3, 2018

(54) METHOD AND COMPUTING DEVICE FOR WINDOW LEVELING BASED UPON A GAZE LOCATION

(71) Applicant: Change Healthcare LLC, Alpharetta, GA (US)

(72) Inventors: Mahmoud Ramze Rezaee, North Vancouver (CA); Clifford Edwards, Delta (CA)

(73) Assignee: CHANGE HEALTHCARE LLC, Alpharetta, GA (US)

( * ) Notice: Subject to any disclaimer, the term of this patent is extended or adjusted under 35 U.S.C. 154(b) by 0 days.

(21) Appl. No.: 14/228,779

(22) Filed: Mar. 28, 2014

(65) Prior Publication Data

US 2015/0277554 A1    Oct. 1, 2015

(51) Int. Cl.
| | |
|---|---|
| G09G 5/00 | (2006.01) |
| G06F 3/01 | (2006.01) |
| G06F 3/14 | (2006.01) |
| G06K 9/32 | (2006.01) |
| G06K 9/00 | (2006.01) |
| G06F 19/00 | (2018.01) |

(52) U.S. Cl.
CPC ............... *G06F 3/013* (2013.01); *G06F 3/14* (2013.01); *G06F 19/3406* (2013.01); *G06K 9/3233* (2013.01); *G06F 19/321* (2013.01); *G06K 9/0061* (2013.01)

(58) Field of Classification Search
CPC ...... G06F 3/013; G06K 9/10061; G06K 9/46; G06K 2009/4666
USPC .......................... 345/156, 684; 382/274, 103
See application file for complete search history.

(56) References Cited

U.S. PATENT DOCUMENTS

| | | | |
|---|---|---|---|
| 8,643,680 B2 * | 2/2014 | Baldwin et al. | 345/684 |
| 2008/0089602 A1 * | 4/2008 | Heath et al. | 382/274 |
| 2016/0063303 A1 * | 3/2016 | Cheung | G06K 9/0061 382/103 |

* cited by examiner

*Primary Examiner* — Kumar Patel
*Assistant Examiner* — Kuo Woo
(74) *Attorney, Agent, or Firm* — Alston & Bird LLP

(57) ABSTRACT

A method, a computing device and a computer program product are provided in order to automatically apply window leveling to an image, such as a medical image. In the context of a method, a gaze location within an image is determined based upon a determination that a user is staring at the gaze location. The method also determines a region of interest within the image based upon the gaze location and determines pixel values for pixels within the region of interest. The method also establishes window level values based upon the pixel values for pixels within the region of interest and applies window leveling based upon the window level values established based upon the pixel values for pixels within the region of interest.

35 Claims, 3 Drawing Sheets

METHOD AND COMPUTING DEVICE FOR WINDOW LEVELING BASED UPON A GAZE LOCATION

TECHNOLOGICAL FIELD

An example embodiment of the present invention relates generally to window leveling and, more particularly, to window leveling based upon a gaze location at which a user is staring.

BACKGROUND

Medical images are captured by a wide variety of modalities including, for example, computerized tomography (CT), magnetic resonance imaging (MRI), computed radiography (CR), digital radiography (DR) and mammography (MG). Regardless of the modality, the medical images are comprised of a plurality of pixels, each of which has a respective pixel value. Each pixel value corresponds to a distinct gray level or a distinct shade of color, such as red, green or blue depending upon the respective color channel. Many modalities, such as each of the foregoing examples, have pixels with a relatively large range of values, thereby defining a dynamic pixel value range. In this regard, the range of pixel values may be substantially greater than the 256 pixel values that most displays are capable of presenting. For example, depending upon whether the image is an original image or has been post-processed, the pixel range of an image could be expressed by 10 bits so as to have 1024 different pixel values, 12 bits so as to have 4096 different pixel values or 16 bits so as to have 65536 different pixel values.

Most displays and most operating systems that support the display of medical images only allow for 256 shades of grey (in an instance in which a grey scale monitor is utilized) or 256 shades of each of red, green and blue colors (in an instance in which a color monitor having red, green and blue color channels is utilized) to be simultaneously displayed. Due to the differences between the dynamic pixel value range and the number of different pixel values that may be simultaneously presented by a display, the dynamic pixel value range may be divided into intervals, each of which has an equal number of different values, e.g., 256 different pixel values, as those which can be simultaneously presented by display. Within the interval of pixel values, the different pixel values are represented by different shades of gray or different shades of color. For pixel values that are below the minimum pixel value of the interval, the pixel values may be mapped to the minimum pixel value of the interval. Similarly, for pixel values that are above the maximum pixel value of the interval, the pixel values may be mapped to the maximum pixel value of the interval.

A user may modify the interval across the full dynamic pixel value range so as to permit the user to view the other pixel values. The interval may be defined in terms of a window and a level. The width of the interval in terms of the range of pixel values is termed a window with the center of the range of pixel values within the window being termed the level. In general, a window may be of any size with the windowing process mapping the pixel value range of the window from [center−width/2, center+width/2] to the nearest integer [0-255] for a display capable of presenting 256 shades. The mapping of the pixel values to the output intensities may be performed in accordance with a function. Depending on the type of function, a group of pixels may map to some grayscale (or color) values or some grayscale (or color) values may not be used at all.

This mapping of pixel values and output intensities is generally termed window leveling. In many modalities, the optimal window level is not known in advance and users must manually modify the window level until a proper value is found. This modification of the window level may be performed by user interaction with an image viewer application, such as a Picture Archiving and Communication System (PACS) viewer, through an input device, such as a mouse. In this regard, a user may modify the window level by moving the window throughout the dynamic pixel value range so as to permit different pixel values to be visualized.

For radiologists, window leveling may be the most interactive tool that they utilize. For many modalities such as CR, DR or MG, the initial value of the window level may be based upon the entire pixel range, e.g., window equals 4096 and level equals 2048. As such, a radiologist may be required to perform substantial window leveling by moving the window through the pixel range until the radiologist is satisfied with the displayed image. The time expended for window leveling may decrease the efficiency with which a radiologist reviews an image and may require at least some skill or experience on the part of the radiologist. Additionally, the window leveling that is performed and is appropriate for one portion of an image may not be ideal for another portion of the image since different portions of the image may include different anatomy with pixels having different ranges of values. Thus, a user may have to repeatedly adjust the window leveling as the user views different portions of the image, thereby further reducing the efficiency with which the user reviews the images.

BRIEF SUMMARY

A method, a computing device and a computer program product are provided in accordance with an example embodiment in order to automatically apply window leveling to an image, such as a medical image. In this regard, the method, computing device and a computer program product of an example embodiment may identify a region of interest within the image based upon a gaze location at which the user is staring with the window leveling being based upon the pixel values for pixels within the region of interest. Thus, the method, computing device and computer program product may automatically adapt the window leveling as the user stares at different portions of the image such that not only is appropriate window leveling provided for the portion of the image that is the subject of the user's attention, but the window leveling is performed in an efficient and automated manner without requiring input by the user other than staring at the gaze location within the image.

In an example embodiment, a method is provided that includes determining a gaze location within an image based upon a determination that a user is staring at the gaze location. The method of this embodiment also determines a region of interest within the image based upon the gaze location and determines pixel values for pixels within the region of interest. The method of this example embodiment also establishes window level values based upon the pixel values for pixels within the region of interest and applies window leveling based upon the window level values established based upon the pixel values for pixels within the region of interest.

The method of an example embodiment may determine the gaze location by determining that the user has stared at the gaze location for at least a predefined period of time. The method may determine the region of interest by determining the region of interest to be centered about the gaze location and to have a predefined shape and a predetermined size. In an example embodiment, the method may apply window leveling by applying the window leveling for only those pixels within the region of interest. The method of an example embodiment may also include setting an input device sensitivity based upon the pixel values for pixels within the region of interest. In regards to applying window leveling, the method of an example embodiment may construct a look up table based upon the window level values and the predefined function and may determine output intensities corresponding to the pixel values for pixels within the region of interest based upon the look up table. The method of an example embodiment may also include determining that the gaze location within the image has changed and, if so, again determining the region of interest, determining pixel values, establishing window level values and applying window leveling for the gaze location following its change.

In another example embodiment, a computing device is provided that includes processing circuitry configured to determine a gaze location within an image based upon a determination that a user is staring at the gaze location. The processing circuitry of an example embodiment may also be configured to determine a region of interest within the image based upon the gaze location and to determine pixel values for pixels within the region of interest. In accordance with this example embodiment, the processing circuitry may also be configured to establish window level values based upon the pixel values for pixels within the region of interest and to apply window leveling based upon the window level values established based upon the pixel values for pixels within the region of interest.

The processing circuitry of an example embodiment may be configured to determine the gaze location by determining that the user has stared at the gaze location for at least a predefined period of time. The processing circuitry of an example embodiment may be configured to determine the region of interest by determining the region of interest to be centered about the gaze location and to have a predefined shape and a predetermined size. In an example embodiment, the processing circuitry is configured to apply window leveling by applying the window leveling for only those pixels within the region of interest. The processing circuitry of an example embodiment may be further configured to set an input device sensitivity based upon the pixel values for pixels within the region of interest. The processing circuitry of an example embodiment may be configured to apply window leveling by constructing a look up table based upon the window level values and the predefined function and then determining output intensities corresponding to the pixel values for pixels within the region of interest based upon the look up table. In an example embodiment, the processing circuitry may be further configured to determine that the gaze location within the image has changed and to again determine the region of interest, determine pixel values, establish window level values and apply window leveling for the gaze location following its change.

In a further embodiment, a computer program product is provided that includes a non-transitory computer readable medium and a program code stored thereon with the program code comprising program code instructions configured, upon execution, to determine a gaze location within an image based upon a determination that a user is staring at the gaze location. The program code of this example embodiment will also include the program code instructions configured to determine a region of interest within the image based upon the gaze location and to determine pixel values for pixels within the region of interest. The program code of this example embodiment also includes program code instructions configured to establish window level values based upon the pixel values for pixels within the region of interest and to apply window leveling based upon the window level values established based upon the pixel values for pixels within the region of interest.

The program code instructions configured to determine the gaze location may include program code instructions configured to determine that the user has stared at the gaze location for at least a predefined period of time. In an example embodiment, the program code instructions configured to determine the region of interest may include program code instructions configured to determine the region of interest to be centered about the gaze location to have a predefined shape and a predetermined size. The program code instructions configured to apply window leveling may, in one embodiment, be configured to apply the window leveling for only those pixels within the region of interest. The program code of an example embodiment may also include program code instructions configured to set an input device sensitivity based upon the pixel values within the region of interest. The program code instructions that are configured to apply window leveling may, in one example embodiment, include program code instructions configured to construct a look up table based upon the window level values and the predefined function and to determine output intensities corresponding to the pixel values for pixels within the region of interest based upon the look up table.

BRIEF DESCRIPTION OF THE DRAWINGS

Figure 1:
Figure 2:
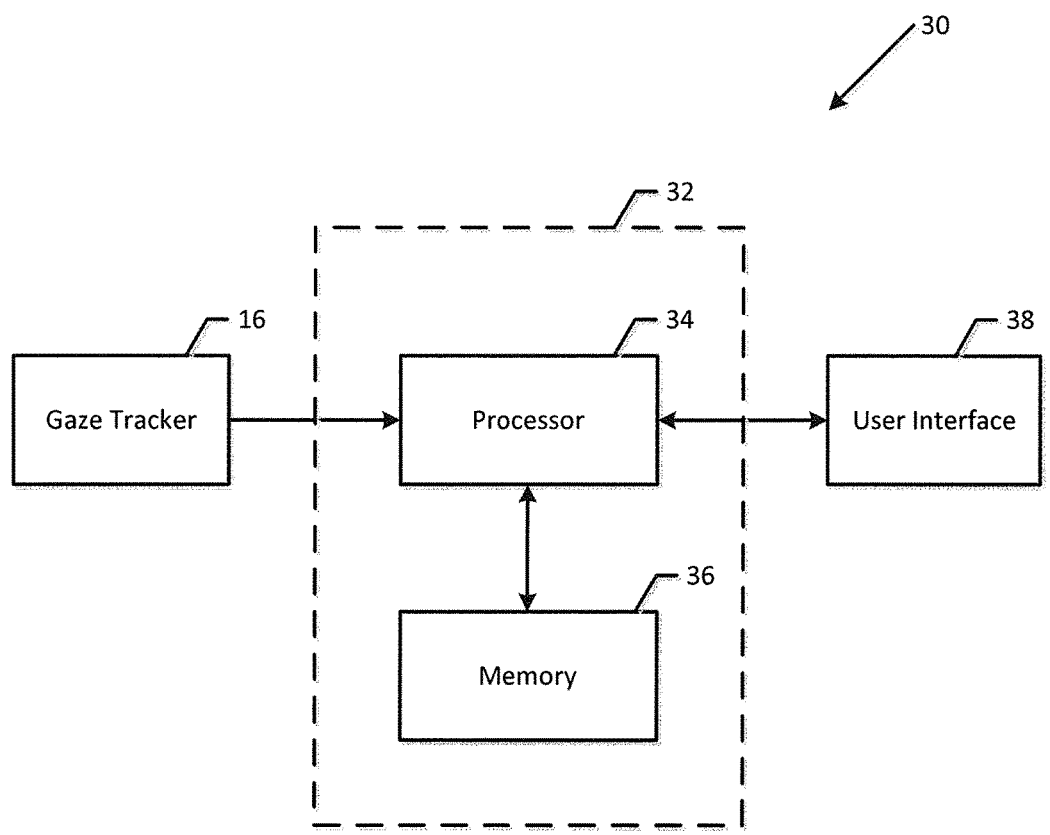
Figure 3:
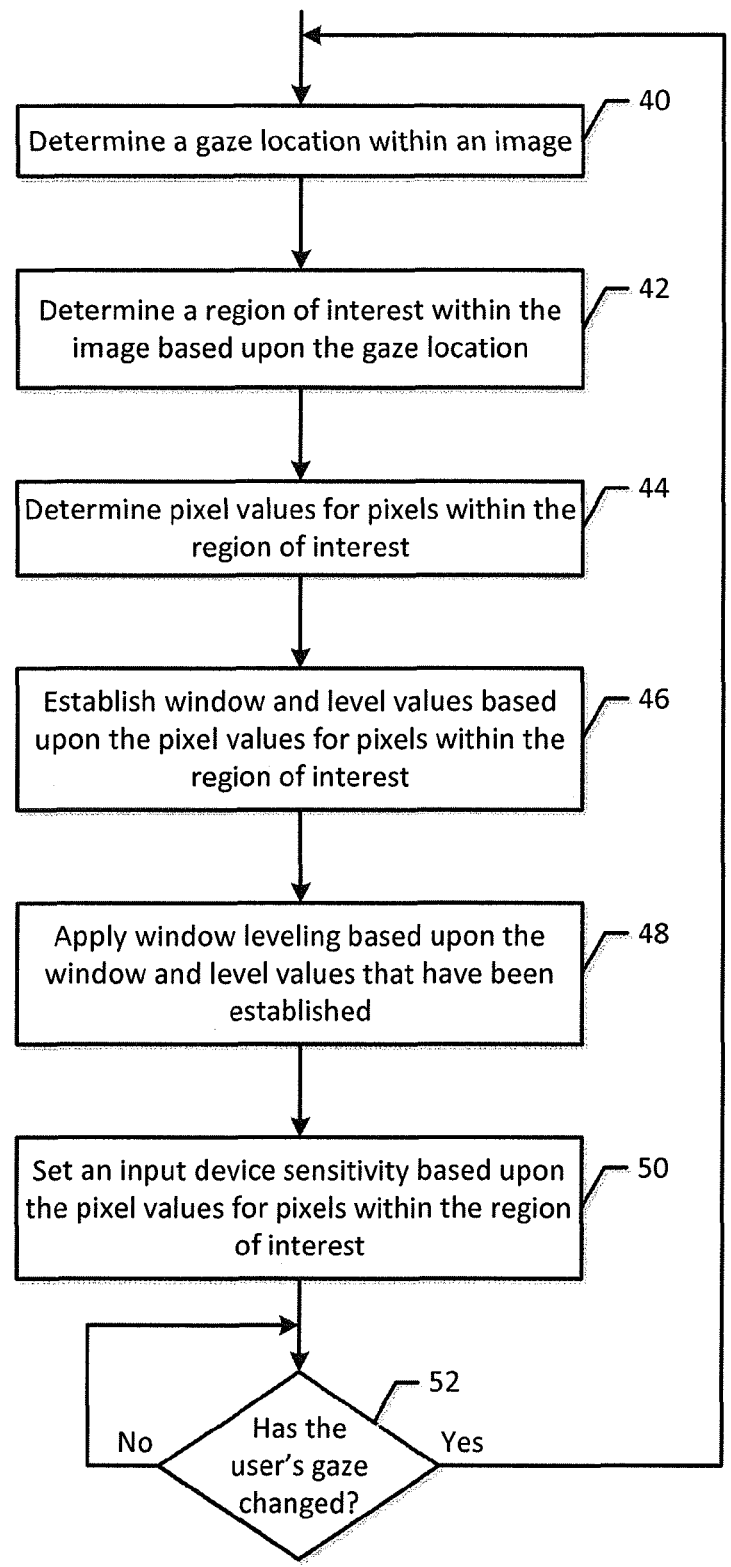

Having thus described example embodiments of the present disclosure in general terms, reference will now be made to the accompanying drawings, which are not necessarily drawn to scale, and wherein:

FIG. 1 is a perspective view of a user viewing an image upon a display and, more particularly, a user staring at a gaze location within the image upon the display;

FIG. 2 is a block diagram of a computing device that may be specifically configured in accordance with an example embodiment of the present invention; and FIG. 3 is a flow chart illustrating operations performed, such as by the computing device of FIG. 2, in accordance with the example embodiment of the present invention.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout. As used herein, the terms "data," "content," "information" and similar terms may be used interchangeably to refer to data capable of being transmitted, received and/or stored in accordance with embodiments of the present invention. Thus, use of any such terms should not be taken to limit the spirit and scope of embodiments of the present invention.

A method, computing device and computer program product are provided according to example embodiments of the present invention in order to provide for window leveling in an automated fashion based upon the gaze location within an image at which the user is staring. By applying window leveling in an automated fashion, the window leveling may be accomplished in a more efficient manner without distracting the user from his or her review of the image. In addition, by basing the window leveling upon the gaze location within the image at which the user is staring, the window leveling may be performed in a manner that is appropriate for that portion of the image that the user is currently reviewing, thereby increasing the precision of the window leveling.

The window leveling may be performed in accordance with a method, computing device and computer program product in a variety of settings and in conjunction with a variety of different types of images. In an example embodiment depicted in FIG. 1, a user may interact with a computing device 10, such as a workstation, a personal computer, an image viewing station, e.g., a PACS station, a tablet computer, a laptop computer or a mobile terminal, e.g., a smartphone, a personal digital assistant (PDA) or the like. Regardless of the manner in which the computing device is instantiated, the computing device may include a display 12 and a keyboard 14 or other type of user interface. As shown in FIG. 1, an image may be presented upon the display. In an example embodiment, the image may be a medical image, such as a medical image captured by any of a wide variety of different modalities, such as CT, MRI, CR, DR or MG modalities. In one embodiment, a radiologist may review the images. However, other types of users, such as other health care practitioners, patients or the like, may view the images. As described below, the gaze location within the image at which the user is staring may be determined with window leveling appropriate for a region of interest surrounding the gaze location being applied in an automated fashion, that is, without manual input.

As shown in FIG. 2, an example embodiment of a computing device 30 that may be specifically configured in accordance with an example embodiment of the present invention is depicted. The computing device of FIG. 2 may be the same computing device that provides for the display of images as shown in FIG. 1. Alternatively, the computing device of FIG. 2 may be distinct from the computing device 10 that provides for the display of the images, but may be in communication therewith so as to apply appropriate window leveling to the images that are presented upon the display 12. As such, the computing device in FIG. 2 may be embodied by PACS workstation, a computer workstation, a personal computer, a tablet computer, a laptop computer, a mobile terminal, such as a smartphone, a PDA or the like. Alternatively, the computing device 30 may be a server or other network-based computing device that interacts with a computer device 10 that presents images upon the display in order to perform certain functionalities, such as to perform window leveling based upon gaze tracking.

Regardless of the manner in which the computing device 30 is embodied, the computing device may include of one embodiment may be generally depicted as shown in FIG. 2 so as to include or to be associated and in communication with processing circuitry 32 that is configurable to perform functions in accordance with one or more example embodiments disclosed herein. In this regard, the processing circuitry may be configured to perform and/or control performance of one or more functionalities of the computing device in accordance with various example embodiments, and thus may provide means for performing functionalities of the computing device. The processing circuitry may be configured to perform data processing, application execution and/or other processing and management services according to one or more example embodiments.

In some example embodiments, the processing circuitry 32 may include a processor 34 and, in some embodiments, such as that illustrated in FIG. 2, may further include memory 36. The processing circuitry may be in communication with or otherwise control a user interface 38, such as a display 12, a keyboard 14 and/or other input/output mechanisms and, in some embodiments, may also optionally include a communication interface for communicating with other computing systems. As such, the processing circuitry may be embodied as a circuit chip (e.g., an integrated circuit chip) configured (e.g., with hardware, software or a combination of hardware and software) to perform operations described herein.

The processor 34 may be embodied in a number of different ways. For example, the processor may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. Although illustrated as a single processor, it will be appreciated that the processor may comprise a plurality of processors. The plurality of processors may be in operative communication with each other and may be collectively configured to perform one or more functionalities of the computing device 30 as described herein. The plurality of processors may be embodied on a single computing device or distributed across a plurality of computing devices collectively configured to function as the computing device. In some example embodiments, the processor may be configured to execute instructions stored in the memory 36 or otherwise accessible to the processor. As such, whether configured by hardware or by a combination of hardware and software, the processor may represent an entity (e.g., physically embodied in circuitry—in the form of processing circuitry 32) capable of performing operations according to embodiments of the present invention while configured accordingly. Thus, for example, when the processor is embodied as an ASIC, FPGA or the like, the processor may be specifically configured hardware for conducting the operations described herein. Alternatively, as another example, when the processor is embodied as an executor of software instructions, the instructions may specifically configure the processor to perform one or more operations described herein.

In some example embodiments, the memory 36 may include one or more non-transitory memory devices such as, for example, volatile and/or non-volatile memory that may be either fixed or removable. In this regard, the memory may comprise a non-transitory computer-readable storage medium. It will be appreciated that while the memory is illustrated as a single memory, the memory may comprise a plurality of memories. The plurality of memories may be embodied on a single computing device or may be distributed across a plurality of computing devices collectively configured to function as the computing device 30. The memory may be configured to store information, data, applications, instructions and/or the like for enabling the computing device to carry out various functions in accordance with one or more example embodiments. For example, the memory may be configured to buffer input data for processing by the processor 34. Additionally or alternatively, the memory may be configured to store instructions for execution by the processor. As yet another alternative, the memory may include one or more databases that may store a variety of files, contents or data sets, such as medical images, e.g., image studies, for a plurality of patients. Among the contents of the memory, applications may be stored for execution by the processor in order to carry out the functionality associated with each respective application. In some cases, the memory may be in communication with one or more of the processor or the user interface 38 via a bus or buses for passing information among components of the computing device.

Having now described a computing device 30 configured to implement and/or support implementation of various example embodiments, features of several example embodiments will now be described. It will be appreciated that the following features are non-limiting examples of features provided by some example embodiments. Further, it will be appreciated that embodiments are contemplated within the scope of disclosure that implement various subsets or combinations of the features further described herein. Accordingly, it will be appreciated that some example embodiments may omit one or more of the following features and/or implement variations of one or more of the following features.

The computing device 30 may include or otherwise be associated or in communication with a gaze tracker 16. A variety of different types of gaze trackers may be utilized in order to determine the location within the image presented upon the display 12 at which the user is staring. For example, the gaze tracker may comprise an eye tracker, such as any of various models of eye trackers provided by Tobii Technology, Inc. As shown in FIG. 1, the gaze tracker may be mounted upon the display so as to capture images of the user that may be processed in order to determine the gaze location within the image at which the user is staring. The gaze tracker may determine the location within the image at which the user is staring with either eye, individually. In an instance in which the user's eyes are focused on the plane of the display, the gaze point is essentially the same for both eyes. Additionally or alternatively, the gaze tracker may determine the locations within the image at which both eyes of the user are staring with the gaze location being defined to be the average or midpoint of those locations.

Referring now to FIG. 3, the operations performed, such as by the computing device 30 of FIG. 2, in order to apply window leveling in an automated fashion based upon a gaze location within an image at which a user is staring are provided. As shown in block 40 of FIG. 3, the computing device, such as the processing circuitry 32, the processor 34, the gaze tracker 16 or the like, may determine the gaze location within the image presented upon the display 12 based upon a determination that a user is staring at the gaze location. In order to ensure that the user is staring at the gaze location, the computing device, such as the processing circuitry, the processor, the gaze locator or the like, may be configured to determine the gaze location only once it has been determined that the user has stared at the same location, i.e., the gaze location, for at least a predefined period of time. In this example embodiment, the gaze location is therefore not identified in an instance in which the user only looks at a particular portion of the image for less than the predefined period of time. The computing device, such as the processing circuitry, the processor, the gaze locator or the like, may be configured to determine the gaze location in other manners. For example, in an instance in which a radiologist is concurrently reviewing two or more images that may be anatomically and/or functionally related. In this example, the radiologist may be glancing back and forth between the images such that the radiologist does not stare at the same location on either of the images for the predefined period of time. However, the computing device, such as the processing circuitry, the processor, the gaze locator or the like, of an example embodiment may be configured to determine that the gaze of the radiologist has most recently been focused upon the same anatomical region as it appears in each of the images and, as such, may determine the gaze location to coincide with that anatomical region. Still further, the computing device, such as the processing circuitry, the processor, the gaze locator or the like, may be configured to determine the gaze location in an instance in which a user does not stare at a particular location within an image for the predefined period of time, but instead, looks at the particular location and then glances away before returning to look at the particular location one or more times. In this example, the computing device, such as the processing circuitry, the processor, the gaze locator or the like, may be configured to determine the gaze dwell time to be the sum of the time that the user is determined to stare at the particular location as the user repeatedly glances at the particular location. In an instance in which the gaze dwell time equals or exceeds a predetermined (or configurable) threshold, which may be the same as or different than the predefined period of time, the computing device, such as the processing circuitry, the processor, the gaze locator or the like, may be configured to determine the gaze location to coincide with the particular location, even though the user has not continuously stared at the particular location for the predefined period of time.

As shown in block 42 of FIG. 3, the computing device 30, such as the processing circuitry 32, the processor 34 or the like, may also be configured to determine a region of interest within the image based upon the gaze location. For example, the region of interest may be centered about the gaze location and may have a predefined shape and a predetermined size. In the example depicted in FIG. 1, the predefined shape of the region of interest 20 is a circle centered about the gaze location 18 and the predetermined size may be the predetermined radius or diameter of the circle. However, the region of interest may have other shapes, such as a square or other rectangular shape, an ellipse or the like, and the predetermined size may be defined in other manners, such as based upon the length of a side of a square or the length of two sides of a rectangle. Although the predefined shape and predetermined size of the region of interest may be fixed or static, the predefined shape and the predetermined size may be configurable by the user and/or subject to dynamic user control, such as via an input mechanism, e.g., an input provided via a keyboard and/or mouse, so as to permit modification of the region of interest.

As set forth in block 44, the computing device 30, such as the processing circuitry 32, the processor 34 or the like, may be configured to determine pixel values for pixels within the region of interest. The computing device, such as the processing circuitry, the processor or the like, may represent the pixel value of the pixels within the region of interest in various manners, such as by determining the minimum pixel value and the maximum pixel value, determining the median or average pixel value and/or determining a histogram representing the distribution of pixel values. The pixel values may represent different grey scale levels for a gray scale image. Alternatively, the pixel values may represent different shades of color, such as different shades of red, green, or blue, for a color image to be presented by a color display.

Based upon the pixel values for pixels within the region of interest, the computing device 30, such as the processing circuitry 32, the processor 34 or the like, may be configured to establish window and level values. See block 46 of FIG. 3. By establishing the window and level values based upon pixel values for pixels within the region of interest, as opposed to pixel values for pixels within the entire image, the range of pixel values for pixels within the region of interest is generally smaller. In some instances, the range of pixel values for pixels within the region of interest is no more than 256, such that the window may include all of the pixel values for pixels within the region of interest. In an instance in which the pixel values for pixels within the region of interest have a range that exceeds 256, the window may be established so as to include the majority of the pixel values or in some other fashion, such as by including the largest pixel values for pixels within the region of interest or the smallest pixel values for pixels within the region of interest. In this embodiment, pixel values that are less than the minimum pixel value of the window may be represented by the minimum pixel value within the window and pixel values that are greater than the maximum value of the window may be represented by the maximum pixel value within the window. Within the window, the level may be established to be the midpoint within the window, such as by determining the difference between the maximum pixel value and the minimum pixel value within the window and then dividing by two.

The computing device 30, such as the processing circuitry 32, the processor 34 or the like, is also configured to determine the type of function that will be applied to the pixel values of the pixels within the region of interest during window leveling in order to produce corresponding output intensities. The function may be a linear function or a non-linear function. Although the user may define the function, the function may be predefined such that the processing circuitry may determine the type of function by reference to the predefined function stored by the memory device 36.

As shown in block 48 of FIG. 3, the computing device 30, such as the processing circuitry 32, the processor 34, the user interface 38 or the like, may be configured to apply window leveling based upon the window and level values that have been established based upon the pixel values for pixels within the region of interest. In addition, the computing device, such as the processing circuitry, the processor or the like, may apply window leveling based upon the function that was previously identified. While window leveling may be applied in various manners, the computing device, such as the processing circuitry, the processor or the like, may construct a look up table based upon the window and level values and the predefined function. The look up table may be stored in memory 36 and may be accessible to the processor. The look up table associates each pixel value within the window with a value of output intensity for the respective pixel. In this regard, the relationship between the pixel values and the resulting output intensities may be defined by the predetermined function, such as a linear and non-linear function.

In this example embodiment, the computing device 30, such as the processing circuitry 32, the processor 34 or the like, may determine the output intensity for a respective pixel based upon the pixel value for the respective pixel and the look up table that correlates a pixel value to a corresponding output intensity based upon the predetermined function. In this regard, the pixel values for each pixel within the region of interest may be determined. The corresponding output intensity for a pixel having the respective pixel value is then determined in accordance with the predetermined function, such as by reference to the look up table. As such, the pixel of display 12 may thereafter be driven in accordance with the desired output intensity.

In one embodiment, the window leveling may be applied for only those pixels within the region of interest. In this embodiment, the pixels of the image outside of the region of interest are not subjected to the same window leveling. Alternatively, the window leveling may be applied to all of the pixels within the image, even though the window and level values have been determined for a subset of the entire image, that is, based upon the pixel values for just those pixels within the region of interest. Additionally, the computing device 30 of an example embodiment may permit the automatic window leveling described above to be selectively activated and deactivated, thereby providing user control of the manner in which window leveling will be performed. Further, in an example embodiment in which the automatic window leveling is provided, the computing device may be configured to also respond to user input that manually performs window leveling. For example, following the automatic establishment of window leveling, the computing device may detect manual input that is intended to perform window leveling and, as such, may override the automatic window leveling and, may, instead, perform window leveling consistent with the manual input.

Although the computing device 30 is described in the foregoing example embodiment to determine a single set of window and level values based upon a region of interest defined by a gaze location and to correspondingly apply a single window leveling to the region of interest, the computing device of another embodiment may be configured to determine a plurality of sets of window and level values based upon a single region of interest defined by a gaze location and to sequentially apply a plurality of window leveling operations to the region of interest based upon the different sets of window and level values. For example, in an instance in which the display 12 is configured to uniquely present a predefined number, e.g., 256, of different pixel values and the range of pixel values in the region of interest exceeds the predefined number, the computing device, such as the processing circuitry 32, the processor 34 or the like, may be configured to establish a plurality of sets of window and level values based upon the single region of interest and to then sequentially apply different window leveling based upon the plurality of sets of window and level values.

By way of example, in an instance in which the maximum and minimum pixel values in the region of interest are 600 and 300, respectively, such that the range of pixel values in the region of interest, i.e., 300, exceeds the predefined number, i.e., 256, of different pixel values that the display 12 is configured to uniquely present, the computing device 30 may determine a plurality of sets of window and level values and then sequentially apply a plurality of window leveling operations to the region of interest based thereupon. For example, the computing device may define each window value to be equal to the predefined number, i.e., 256, of different pixel values that the display is configured to uniquely present. However, the level and, therefore, the position of the window within the range of pixel values may vary. Initially, the computing device may define the level to be the sum, e.g., 428, of the minimum pixel value in the region of interest, e.g., 300, and the midpoint of the window, e.g., 256/2, in this example. The computing device may then apply window leveling in accordance with a window value of 256 and a level value of 428 for a predetermined time period, e.g., 0.1 seconds. Thereafter, the computing device may incrementally increase the level and apply window leveling in accordance with a window value of 256 and the new level value for the predetermined time period. This process may be repeated, such as for level values of 430, 431, 432, ... 470, 471, 472, until the maximum pixel value is included in the window at a level value of 472. The computing device may then incrementally decrease the level and apply window leveling in accordance with a window value of 256 and the new level value for the predetermined time period. This process may be repeated, such as for level values of 472, 471, 470 ... 430, 429, 428, until the initial level value, e.g., 428, is reached. Subsequently, the computing device can repeat the process of incrementally increasing and then decreasing the level value while the user continues to maintain the same location, or until the user provides input indicated that the automatic window leveling should be paused or discontinued.

The computing device 30 of an example embodiment may also optionally set the input device sensitivity based upon the pixel values for pixels within the region of interest. See block 50 of FIG. 3. While the sensitivity of various different types of input devices may be set, the input device of an example embodiment may be a mouse such that the computing device may optionally set the mouse sensitivity based upon the pixel values for pixels within the region of interest. The input device sensitivity may be set in various manners, but, in one example embodiment, the input device has a predefined range of sensitivity values, such as from a level 1 at which the mouse is most sensitive to a level 20 in which the mouse is least sensitive. The computing device, such as the processing circuitry 32, the processor 34 or the like, may be configured to determine the distribution of the pixel values for pixels within the region of interest and may set the input device sensitivity based upon the distribution of the pixel values. For example, in an instance in which the pixel values of the pixels within the region of interest are closely spaced, e.g., a narrow distribution, the input device sensitivity may be set to a lower sensitivity value, while for pixel values for pixels within the region of interest that are more separated or less closely spaced, e.g., a broader distribution, the input device sensitivity may be set a greater sensitivity value. Thus, the input device sensitivity may bear an inverse relationship, such as an inverse proportional relationship, to the spacing between, e.g., distribution of, the pixel values for pixels within the region of interest.

As indicated by block 52 of FIG. 3, the computing device 30, such as the processing circuitry 32, the processor 34, the gaze tracker 16 or the like, may continue to monitor the gaze location at which the user is staring. In an instance in which the gaze location has changed, the foregoing process may be repeated based upon the new, e.g., the current, gaze location and a predefined region of interest centered thereabout. By determining the region of interest based upon the new gaze location, the window and level values may differ from those previously established such that the window leveling that is applied based upon those window and level values for the region of interest centered about the new gaze location is appropriate for the new gaze location, even though it may differ somewhat from the window leveling applied to the prior gaze location as a result of the different pixel values for pixels within the respective regions of interest.

By way of example, a physician may open the CR study of a patient and may begin looking at the chest anteroposterior (AP) image. Based upon a report of a referring physician who ordered the examination, the patient has recently developed mild shortness of breath and sometimes feels some discomfort in his left lung. The physician wants to determine if these are symptoms of a silent pneumothorax. After a quick initial scan for the overall image quality of the entire image, the physician may stare at the top edge of the left lung for about two seconds. In an instance in which the predefined period of time is two seconds, the gaze detector 16 in combination with the computing device 30 may determine the gaze location which, in turn, defines the center of the region of interest. In an instance in which the predefined shape is a circle and the predetermined size is a diameter of 30 pixels, the computing device, such as the processing circuitry 32, the processor 34 or the like, may determine the pixel values within the circular region of interest. In one example embodiment, the computing device, such as the processing circuitry, the processor or the like, may determine the minimum and maximum pixel values for pixels within the region of interest. As such, the computing device, such as the processing circuitry, the processor or the like, may determine the window to be the maximum pixel value minus the minimum pixel value and may define the level to be the minimum pixel value plus the width of the window divided by two.

In an embodiment in which a linear function is utilized to map pixel values into grey scale levels, output intensities for each of the pixel values of the pixels within the region of interest may be determined. In this regard, a linear look up table may be constructed by the computing device 30, such as the processing circuitry 32, the processor 34 or the like, and the pixel values may be modified in accordance with the look up table so as to apply window leveling to the region of interest, if not the entire image. The physician may be unaware of the image processing that occurs while he stares at the gaze location, but the physician simply knows that after about two seconds, the image contrast at the edge of the left lung may change drastically so as to permit better visibility. Additionally, the sensitivity of the mouse may be modified based upon the pixel values of the pixels within the region of interest. In an instance in which the pixel values within the region of interest are relatively closely spaced, the sensitivity of the mouse may be modified so as to be less sensitive, thereby facilitating relatively minor modifications of the visibility of the soft tissue at the edge of the left lung.

As described above, FIG. 3 is a flowchart of a method, computing device 30 and computer program product according to example embodiments of the invention. It will be understood that each block of the flowchart, and combinations of blocks in the flowchart, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices 36 of a computing device and executed by processing circuitry 32 in the computing device. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s). The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks or steps of the flowchart support combinations of means for performing the specified functions and combinations of steps for performing the specified functions. It will also be understood that one or more blocks of the flowchart, and combinations of blocks in the flowchart, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processing circuitry 32 may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method comprising:
    determining a gaze location within an image based upon a determination that a user is staring at the gaze location;
    determining a region of interest within the image based upon the gaze location;
    determining pixel values for pixels within the region of interest, wherein different pixel values represent different grey scale levels or different shades of color;
    for the image, establishing, with processing circuitry, a plurality of different sets of window and level values based upon the pixel values for pixels within the region of interest, wherein the window defines a range of pixel values to be presented and the level defines a predefined pixel value within the window; and
    sequentially applying window leveling to the region of interest during display of the image based upon different sets of the window and level values established based upon the pixel values for pixels within the region of interest, wherein sequentially applying window leveling comprises sequentially varying the level in order to reposition the window and to cause the pixels within the region of interest within the image to have pixel values from within a different range of pixel values such that the image that is displayed has the pixels of the region of interest within the image differently driven as the window leveling causes different sets of window and level values to be sequentially applied to the region of interest.

2. A method according to claim 1 wherein determining the gaze location comprises determining that the user has stared at the gaze location for at least a predefined period of time.

3. A method according to claim 1 wherein determining the region of interest comprises determining the region of interest to be centered about the gaze location and to have a predefined shape and a predetermined size.

4. A method according to claim 1 wherein applying window leveling comprises applying the window leveling for only those pixels within the region of interest.

5. A method according to claim 1 further comprising setting a mouse sensitivity based upon the pixel values for pixels within the region of interest.

6. A method according to claim 1 wherein applying window leveling comprises:
    constructing a look up table based upon the window and level values and a predefined function; and
    modifying the pixel values for pixels within the region of interest based upon the look up table.

7. A method according to claim 1 further comprising determining that the gaze location within the image has changed, wherein determining the region of interest, determining pixel values, establishing window and level values and applying window leveling are performed again for the gaze location following its change.

8. A method according to claim 1 wherein establishing the plurality of different sets of window and level values comprises establishing the plurality of sets of window and level values having the same window value and different level values.

9. A method according to claim 8 wherein sequentially applying window leveling comprises sequentially incrementing or decrementing the level value.

10. A method according to claim 1 wherein determining the gaze location comprises determining, in an instance in which the user alternately views two or more images, that the user is focused on a same anatomical feature in the two or more images.

11. A method according to claim 1 wherein determining the gaze location comprises determining, in an instance in which the user repeatedly views the image, a gaze dwell time, and wherein determining the gaze dwell time comprises summing time expended by the user staring at the gaze location of the image.

12. A method according to claim 1 further comprising setting a sensitivity of an input device based upon the pixel values for pixels within the region of interest.

13. A method according to claim 12 wherein setting the sensitivity comprises setting the sensitivity so as to have an inverse relationship to spacing of pixel values in the region of interest.

14. A method according to claim 1 wherein the level is defined as a midpoint of the range of pixel values that define the window.

15. A computing device comprising processing circuitry configured to:
   determine a gaze location within an image based upon a determination that a user is staring at the gaze location;
   determine a region of interest within the image based upon the gaze location;
   determine pixel values for pixels within the region of interest, wherein different pixel values represent different grey scale levels or different shades of color;
   for the image, establish a plurality of different sets of window and level values based upon the pixel values for pixels within the region of interest, wherein the window defines a range of pixel values to be presented and the level defines a predefined pixel value within the window; and
   sequentially apply window leveling to the region of interest during display of the image based upon different sets of the window and level values established based upon the pixel values for pixels within the region of interest, wherein sequentially applying window leveling comprises sequentially varying the level in order to reposition the window and to cause the pixels within the region of interest within the image to have pixel values from within a different range of pixel values such that the image that is displayed has the pixels of the region of interest within the image differently driven as the window leveling causes different sets of window and level values to be sequentially applied to the region of interest.

16. A computing device according to claim 15 wherein the processing circuitry is configured to determine the gaze location by determining that the user has stared at the gaze location for at least a predefined period of time.

17. A computing device according to claim 15 wherein the processing circuitry is configured to determine the region of interest by determining the region of interest to be centered about the gaze location and to have a predefined shape and a predetermined size.

18. A computing device according to claim 15 wherein the processing circuitry is configured to apply window leveling by applying the window leveling for only those pixels within the region of interest.

19. A computing device according to claim 15 wherein the processing circuitry is further configured to set a mouse sensitivity based upon the pixel values for pixels within the region of interest.

20. A computing device according to claim 15 wherein the processing circuitry is configured to apply window leveling by:
   constructing a look up table based upon the window and level values and a predefined function; and
   modifying the pixel values for pixels within the region of interest based upon the look up table.

21. A computing device according to claim 15 wherein the processing circuitry is further configured to determine that the gaze location within the image has changed, wherein the processing circuitry is configured to again determine the region of interest, determine pixel values, establish window and level values and apply window leveling for the gaze location following its change.

22. A computing device according to claim 15 wherein the processing circuitry is configured to establish the plurality of different sets of window and level values by establishing the plurality of sets of window and level values having the same window value and different level values.

23. A computing device according to claim 22 wherein the processing circuitry is configured to sequentially apply window leveling by sequentially incrementing or decrementing the level value.

24. A computing device according to claim 15 wherein the processing circuitry is configured to determine the gaze location by determining, in an instance in which the user alternately views two or more images, that the user is focused on a same anatomical feature in the two or more images.

25. A computing device according to claim 15 wherein the processing circuitry is configured to determine the gaze location by determining, in an instance in which the user repeatedly views the image, a gaze dwell time, and wherein the processing circuitry is configured to determine the gaze dwell time by summing time expended by the user staring at the gaze location of the image.

26. A computing device according to claim 15 wherein the processing circuitry is further configured to set a sensitivity of an input device based upon the pixel values for pixels within the region of interest.

27. A computing device according to claim 26 wherein the processing circuitry is configured to set the sensitivity by setting the sensitivity so as to have an inverse relationship to spacing of pixel values in the region of interest.

28. A computing device according to claim 15 wherein the level is defined as a midpoint of the range of pixel values that define the window.

29. A computer program product comprising a non-transitory computer readable medium having program code stored thereon, the program code comprising program code instructions configured, upon execution, to:
   determine a gaze location within an image based upon a determination that a user is staring at the gaze location;
   determine a region of interest within the image based upon the gaze location;
   determine pixel values for pixels within the region of interest, wherein different pixel values represent different grey scale levels or different shades of color;
   for the image, establish a plurality of different sets of window and level values based upon the pixel values for pixels within the region of interest, wherein the window defines a range of pixel values to be presented and the level defines a predefined pixel value within the window; and
   sequentially apply window leveling to the region of interest during display of the image based upon different sets of the window and level values established based upon the pixel values for pixels within the region of interest, wherein sequentially applying window leveling comprises sequentially varying the level in order to reposition the window and to cause the pixels within the region of interest within the image to have pixel values from within a different range of pixel values such that the image that is displayed has the pixels of the region of interest within the image differently driven as the window leveling causes different sets of window and level values to be sequentially applied to the region of interest.

30. A computer program product according to claim 29 wherein the program code instructions configured to determine the gaze location comprise program code instructions configured to determine that the user has stared at the gaze location for at least a predefined period of time.

31. A computer program product according to claim 29 wherein the program code instructions configured to determine the region of interest comprise program code instructions configured to determine the region of interest to be centered about the gaze location and to have a predefined shape and a predetermined size.

32. A computer program product according to claim 29 wherein the program code instructions configured to apply window leveling comprise program code instructions configured to apply the window leveling for only those pixels within the region of interest.

33. A computer program product according to claim 29 wherein the program code further comprises program code instructions configured to set a mouse sensitivity based upon the pixel values for pixels within the region of interest.

34. A computer program product according to claim 29 wherein the program code instructions configured to apply window leveling comprise program code instructions configured to:
 construct a look up table based upon the window and level values and a predefined function; and
 modify the pixel values for pixels within the region of interest based upon the look up table.

35. A computer program product according to claim 29 wherein the level is defined as a midpoint of the range of pixel values that define the window.

* * * * *